United States Patent
Brotchie et al.

(10) Patent No.: US 7,935,718 B2
(45) Date of Patent: May 3, 2011

(54) TREATMENT OF DYSKINESIA

(75) Inventors: Jonathan Brotchie, Manchester (GB); Michael Hill, Oldham (GB); Alan Crossman, Manchester (GB)

(73) Assignee: Motac Neuroscience Limited, Manchester (GB)

( * ) Notice: Subject to any disclaimer, the term of this patent is extended or adjusted under 35 U.S.C. 154(b) by 908 days.

(21) Appl. No.: 10/974,980

(22) Filed: Oct. 28, 2004

(65) Prior Publication Data

US 2005/0245587 A1    Nov. 3, 2005

Related U.S. Application Data

(63) Continuation of application No. 10/110,960, filed as application No. PCT/GB00/04046 on Oct. 20, 2000, now abandoned.

(51) Int. Cl.
*A61K 31/415* (2006.01)
(52) U.S. Cl. .................................................... 514/385
(58) Field of Classification Search ............... 514/385
See application file for complete search history.

(56) References Cited

U.S. PATENT DOCUMENTS

| | | |
|---|---|---|
| 4,767,778 A | 8/1988 | Arrang |
| 4,816,456 A | 3/1989 | Summers |
| 5,091,428 A | 2/1992 | Pascal |
| 5,463,074 A | 10/1995 | Shih |
| 5,821,259 A | 10/1998 | Theoharides |
| 5,965,571 A | 10/1999 | Hutchinson |
| 6,136,559 A | 10/2000 | Lovenberg et al. |
| 6,316,475 B1 | 11/2001 | Bennani |
| 6,455,536 B1 | 9/2002 | Brotchie |
| 6,740,659 B2 | 5/2004 | Brotchie |
| 2004/0057956 A1 | 4/2004 | Brotchie et al. |
| 2004/0067956 A1 | 4/2004 | Brotchie |
| 2005/0009856 A1 | 1/2005 | Brotchie |
| 2005/0261282 A1 | 11/2005 | Crossman et al. |
| 2006/0069039 A1 | 3/2006 | Crossman et al. |

FOREIGN PATENT DOCUMENTS

| | | |
|---|---|---|
| WO | 98/44118 | 10/1998 |
| WO | 00 20011 A | 4/2000 |

OTHER PUBLICATIONS

Ingram N.A.W, Newgreen D.B.; "The Use of Tacrine for Tardive Dyskinesia"; American Journal of Psychiatry, vol. 140, No. 31, 1983, pp. 16-29, XP000989784.

JL Juncos et al; "Cholinergic Strategies in T Tourette Synorome: An Open-Label Trial of Tacrine Hydrochloride" Neurology, US, Lippincott Williams & Wilkins, Philadelphia, vol. 48, No. 3, Mar. 1, 1997, p. A397, XP002087141.

Chiavegatto, Silvana et al; "Histamine and Spontaneous Motor Activity: Biphasic Changes, Receptors Involved and Participation of the Striatal Dopamine System" LIFE SCI, 1998, 62(20), 1875-1888, XP000989725.

Sakai n. et al; "Effects of Thioperamide, A Histamine H3 Receptor Antagonish, on Locomotor Activity and Brain Histamine Content in MAST Cell-Deficient W/WV Mice"; Life Sciences, GB, Peramon Press, Oxford, vol. 48, No. 25, 1991, pp. 2397-2404, XP002042695.

(Continued)

*Primary Examiner* — San-ming Hui
(74) *Attorney, Agent, or Firm* — Swanson & Bratschun, L.L.C.

(57) ABSTRACT

The present invention relates to the use of compounds that enhance $H_3$-histamine receptor activity, or activation (e.g. $H_3$-histamine receptor agonists) for the treatment of dyskinesia. The compounds are particularly useful for treating dyskinesia associated with parkinsonian therapy.

23 Claims, 2 Drawing Sheets

OTHER PUBLICATIONS

Figure 1:
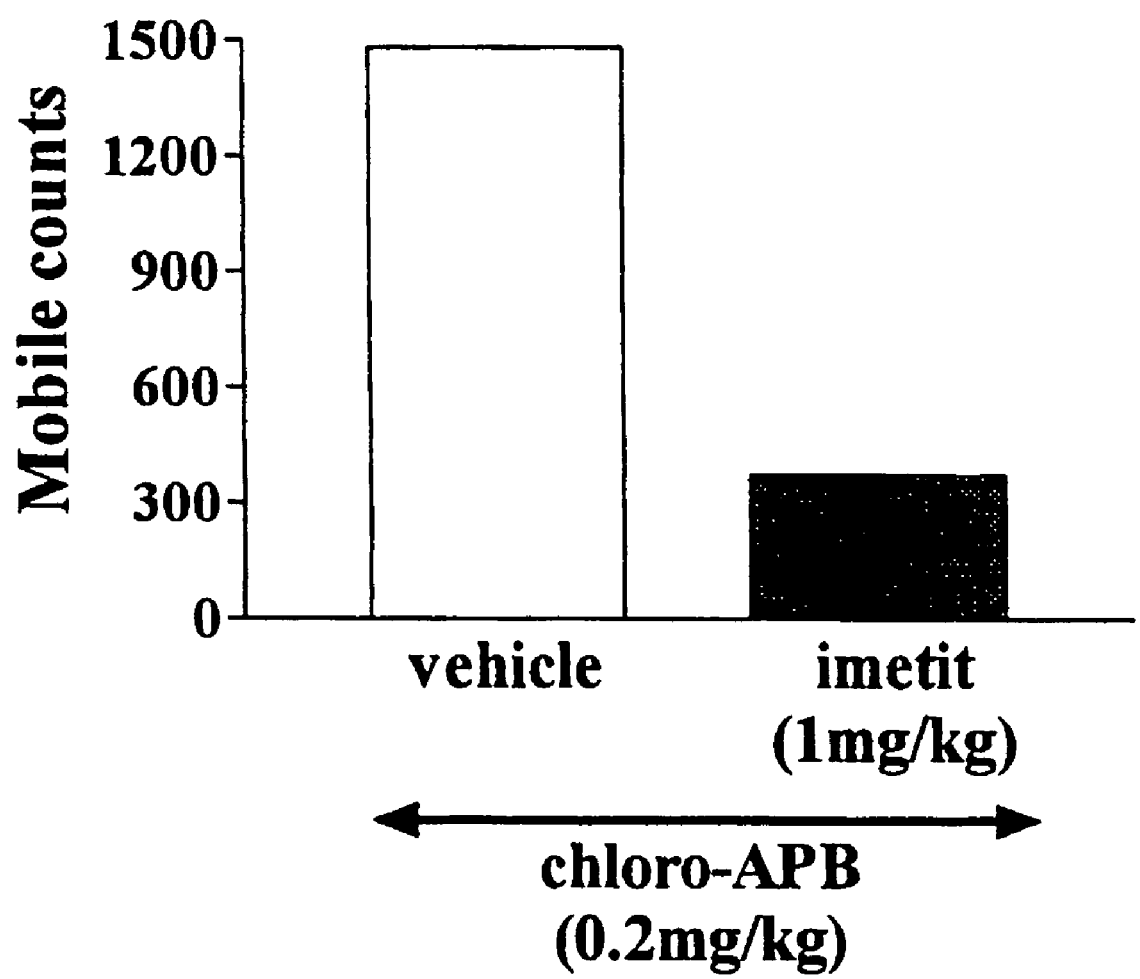

Itoh, Yoshinori et al; "Neuronal Histamine Inhibits Methamphetamine-Induced Locomotor Hyperactivity in Mice"; Neurosci, LETT, 1984, 48(3), 305-9, XP000989775.

Huotari M et al; "Effects of Histamine H-3-Ligand on the Levodopa-Induced Turning Behavior of Hemiparkinsonian Rates"; Parkinsonism & Related Disorders, Jul. 2000, vol. 6, No. 3, pp. 159-164; Publisher: Elsevier Sci Ltd, The Boulevard, Langford Lane, Kidlington, Oxford OX 5 1GB, Oxon, England, ISSN: 1353-8020; XP000989734.

Hill M P et al; "Histamine H3 Receptors Modulate Dopamine D1 Receptor-Dependent Locomotion in the Reserpine-Treated Rat Model of Parkinson's Disease"; Society for Neuroscience Abstracts, vol. 25, No. 1-2, 1999, p. 171; XP000989999.

Schunack and Stark, "Design of Histamine $H_3$-Receptor Agonists and Antagonists", European Journal of Drug Metabolism and Pharmacokinetics 3:173-178 (1994).

Lovenberg et al, "Cloning of Rat Histamine H3 Receptor Reveals Distinct Species Pharmacological Profiles", The Journal of Pharmacology and Experimental Therapeutics 293(3):771-778 (2000).

Leurs et al, "Therapeutic potential of histamine H3 receptor agonists and antagonists", TiPS 19:177-183 (1998).

Timmerman, "Histamine H3 ligands: just pharmacological tools or potential therapeutic agents?", Journal of Medicinal Chemistry 33(1):4-11 (1990).

Leurs et al, "Molecular Pharmacological Aspects of Histamine Receptors", Pharmac. Ther. 66(3):413-463 (1995).

Hill, "Distribution, Properties, and Functional Characteristics of Three Classes of Histamine Receptor", Pharmacological Reviews 42(1):45-83 (1990).

Kathmann et al, "Nordimaprit, homodimaprit, clobenpropit and imetit: affinities for H3 binding sites and potencies in a functional H3 receptor model", Arch Pharmacol. 348: 498-503 (1993).

Lipp et al, "Synthesis, absolute configureation, stereoselectivity, and receptor selectivity of (.alpha.R,.beta.S)-.alpha.,.beta.-dimethylhistamine. A novel highly potent histamine H3 receptor agonist", J. Med. Chem. 35(23):4434-4441 (1992).

Hill et al, "Levetiracetam Potentiates the Antidyskinetic Action of Amantadine in the 1-Methy1-4-pheny1-1,2,3,6-tetrahydropyridine (MPTP)-Lesioned Primate Model of Parkinson's Disease", The Journal of Pharmacology and Experimental Therapeutics 310(1):386 (2004).

Henry et al, "µ- and δ-Opioid Receptor Antagonists Reduce Levodopa-Induced Dyskinesia in the MPTP-Lesioned Primate Model of Parkinson's Disease", Experimental Neurology 171:139-146 (2001).

Danysz et al, "Aminoadamantanes as NMDA Receptor Antagonists and Antiparkinsonian Agents—Preclinical Studies", Neuroscience and Biobehavioral Reviews 21(4):455-468 (1997).

Allen (1998) European Journal of Pharmacology 361:261-268, "Agonist and antagonist effects of histamine H receptor ligands on 3 5-HT receptor-mediated ion currents in NG108-15 cells".

Arrang, et al. (1985) European Journal of Pharmacology 117:109-114, "Stereoselectivity of the Histamine $H_3$-Presynaptic Autoreceptor".

De Esch, et al. (1999) Journal of Medicinal Chemistry 42(7):1115-1122, "Characterization of the Binding Site of the Histamine $H_3$ Receptor. 1. Various Approaches to the Synthesis of 2-(1H-Imidazol-4-yl)cyclopropylamine and Histaminergic Activity of (1R,2R)- and (1S,2S)-2-(1H-Imidazol-4-yl)-cyclopropylamine".

Gomez-Ramirez, et al. (2006) Movement Disorders 21(6):839-846, "Histamine H3 Receptor Agonists Reduce L-Dopa-Induced Chorea, but Not Dystonia, in the MPTP-Lesioned Nonhuman Primate Model of Parkinson's Disease".

International Search Report, PCT/GB00/04046, dated Mar. 27, 2001.

Jablonowski, et al. (2003) J. Med. Chem. 46:3957-3960, "The First Potent and Selective Non-Imidazole Human Histamine H4 Receptor Antagonists".

Kathmann, et al. (1993) Naunyn-Schmiedeberg's Arch Pharmacol 348:498-503, "Nordimaprit, homodimaprit, clobenpropit and imetit: affinities for $H_3$ binding sites and potencies in a functional $H_3$ receptor model".

Krause, et al. (May 12, 2007) "Medicinal chemistry of histamine $H_3$ receptor agonists" Website [Online] Available Web Site: http://www.sciencedirect.com/science?_ob=ArticleURL&_udi=B8GX3-4NPX535-D&_user=10&_coverDate=12%2F31%2F1998&_rdoc=1&_fmt=high&_orig=search&_origin=search&_sort=d&_docanchor=&view=c&_searchStrId=1518064147&_rerunOrigin=google&_acct=C000050221&_version=1&_urlVersion=0&_userid=10&md5=53 8d5dfcf6f4d31213049be9d0c4b6ea&searchtype=a; Last Update: Unknown; Accessed on: Oct. 28, 2010.

Leurs, et al. (1995) British Journal of Pharmacology 116:2135-2321, "Evaluation of the receptor selectivity of the H3 receptor antagonists, iodophenpropit and thioperamide: an interaction with the 5-HT3 receptor revealed".

Leurs, et al. (1995) Pharmac. Ther. 66(3):413-463, "Molecular Pharmacological Aspects of Histamine Receptors".

Leurs, et al. (1998) TiPS 19:177-183, "Therapeutic potential of histamine $H_3$ receptor agonists and antagonists".

Lipp, et al. (1992) J. Med. Chem. 35(23):4434-4441, "Synthesis, absolute configuration, stereoselectivity, and receptor selectivity of (αR,βS)-α,β-dimethylhistamine, a novel highly potent histamine $H_3$ receptor agonist".

Lovenberg, et al. (2000) The Journal of Pharmacology and Experimental Therapeutics 293(3):771-778, "Cloning of Rat Histamine $H_3$ Receptor Reveals Distinct Species Pharmacological Profiles".

Nguyen, et al. (2001) Molecular Pharmacology 59:427-433, "Discovery of a Novel Member of the Histamine Receptor Family".

Nickel, et al. (2001) Br J Pharmacol. 132(8):1665-1672, "Novel histamine $H_3$-receptor antagonists and partial agonists with a non-aminergic structure".

Shih, et al. (1995) J. Med. Chem. 38:1593-1599, "A Novel Pyrrolidine Analog of Histamine as a Potent, Highly Selective Histamine H3 Receptor Agonist".

Shih, et al. (1998) Bioorganic & Medicinal Chemistry Letters 8:243-248, "Trans-4-Methyl-3-Imidazoyl Pyrrolidine as a Potent, Highly Selective Histamine $H_3$ Receptor Agonist In Vivo".

Stark, et al. (1996) European Journal of Pharmaceutical Sciences, 4(1):S117, "Prodrug Developments on Histamine H3-Receptor Agonists".

van der Goot & Timmerman (2000) Eur. J. Med. Chem. 35:5-20, "Selective ligands as tools to study histamine receptors".

Timmerman (1990) J. Med. Chem. 33(1):4-11, Histamine $H_3$ ligands: just pharmacological tools or potential therapeutic agents?

TREATMENT OF DYSKINESIA

This application is a continuation of application Ser. No. 10/110,960, filed May 30, 2002, now abandoned which is the U.S. national phase of international application PCT/GB00/04046 filed on 20 Oct. 2000, which designated the U.S. and claims priority to GB application No. 9924941.9, filed 22 Oct. 1999. The entire contents of these applications are incorporated herein by reference.

The present invention relates to the treatment of dyskinesia.

Dyskinesias are characterised by the development in a subject of abnormal involuntary movements and may manifest as chorea (irregular, involuntary movements of the body, especially the face and extremities) or dystonia (disorder or lack of muscle tonicity).

One way in which dyskinesias may arise is as a side effect of dopamine replacement therapy for Parkinsonism or other basal ganglia-related movement disorders. Parkinsonism is a syndrome of symptoms characterised by slowness of movement (bradykinesia), rigidity and/or tremor. Parkinsonian symptoms are seen in a variety of conditions, most commonly in idiopathic parkinsonism (i.e. Parkinson's Disease) but also following treatment of schizophrenia, manganese poisoning, head injury and the like.

The use of dopamine-replacing agents (e.g. L-DOPA and apomorphine) as symptomatic treatments for conditions such as Parkinson's disease have undoubtedly been successful in increasing the quality of life of patients suffering from the conditions. However, dopamine-replacement therapy does have limitations, especially following long-term treatment. Problems can include a wearing-off of the anti-parkinsonian efficacy of the treatment and in particular the appearance of a range of side effects. These side effects may manifest as dyskinesias such as chorea and dystonia. Dyskinesia can be seen either when the patient is undergoing dopamine-replacement therapy (in the case of chorea and/or dystonia) or even when off therapy (when dystonia is prevalent). Ultimately, these side-effects severely limit the usefulness of dopaminergic treatments.

Many attempts have been made to develop agents that will prevent the development of, and/or treat, dyskinesias. For instance, attempts have been made to develop novel dopamine replacement therapies that will obviate or mitigate dyskinetic side effects although such attempts have met with limited success. There is therefore a need to develop ways by which dyskinesias may be treated.

According to a first aspect of the present invention, there is provided a use of a compound which enhances $H_3$-histamine receptor activity, or activation, for the manufacture of a medicament for the treatment of dyskinesia.

According to a second aspect of the present invention, there is provided a composition for use in the treatment of dyskinesia comprising a therapeutically effective amount of a compound which enhances $H_3$-histamine receptor activity, or activation, and a pharmaceutically acceptable vehicle.

According to a third aspect of the present invention, there is provided a method for the treatment of dyskinesia comprising administering to a person or animal in need of such treatment a therapeutically effective amount of a compound which enhances $H_3$-histamine receptor activity, or activation.

$H_3$-histamine receptors are a subclass of histamine receptors which are found in neural tissues.

By "dyskinesia" we mean the development in a subject of abnormal involuntary movements. These movements may manifest as chorea (irregular, involuntary movements of the body, especially the face and extremities) or dystonia (disorder or lack of muscle tonicity). Such movements include ballistic movements and athetoid movements of the trunk, limbs and facial musculature.

The invention is based upon our studies relating to the neural mechanisms underlying movement disorders. Although we do not wish to be bound by any hypothesis, we believe that movement disorders involve abnormal activity of basal ganglia output pathways and in many cases this is brought about by abnormal function of striatal efferent pathways. These consist of a "direct" pathway to the medial or internal segment of the globus pallidus and the pars reticulata of the substantia nigra and a "indirect" pathway to the lateral or external segment of the globus pallidus. One of the pathophysiological hallmarks of dyskinesia is overactivity of the direct striatal output pathway (In L-DOPA induced dyskinesia, this overactivity appears in part to be caused by an overstimulation of dopamine $D_1$-receptors). We believe compounds which enhance $H_3$-histamine receptor activity, or activation reduce the activity of the striatal output pathway and thereby reduce dyskinesia.

We have found that compounds which enhance $H_3$-histamine receptor activity, or activation are highly effective for the treatment of dyskinesias. For instance, we have found that dyskinesias (e.g. chorea and dystonia) do not develop, or are at least reduced, when the compounds are given to subjects on dopamine-replacement therapy for the treatment of a movement disorder.

Several classes of compound, which may be used according to the invention, are capable of enhancing $H_3$-histamine receptor activity. These compounds include:
  (i) $H_3$-histamine receptor agonists and partial agonists;
  (ii) compounds which enhance synthesis of endogenous $H_3$-histamine receptor agonists (e.g. histamine per se);
  (iii) compounds which enhance release of $H_3$-histamine receptor agonists;
  (v) compounds which block the rate of inactivation or metabolism of $H_3$-histamine receptor agonists (e.g. histamine-N-methyltransferase inhibitors such as 9-amino-1,2,3,4-tetrahydroacridine and SKF91488); and
  (vi) compounds which promote/increase $H_3$-histamine receptor expression and/or transcription.

The compound may modulate any type of histamine receptor provided that $H_3$-histamine receptor activity is enhanced (e.g. histamine per se may be used as an example of a $H_3$-histamine receptor agonist.). However it is preferred that the compound selectively enhances the activity of $H_3$-histamine receptors. By "selectively" we mean the compound enhances $H_3$-histamine receptor activity or activation to a greater extent than other types of histamine receptor (e.g. $H_1$- or $H_2$-receptors).

$H_3$-histamine receptor agonists ((i) above) are preferred compounds for use according to the invention. Selective $H_3$-histamine receptor agonists which are suitable for treating dyskinesias include Imetit, Imepip and R(-)-alpha-methylhistamine. One parameter by which selectivity of $H_3$ agonists may be assessed is by comparing binding affinities of a particular compound for each subclass of a receptor. Preferred selective $H_3$ agonists have a higher binding affinity for the $H_3$ receptor than for the $H_1$ and $H_2$ receptors.

The compounds (and compositions or medicaments containing them) may be used to treat many types of dyskinesia. For instance the compounds may be used to treat dyskinesia associated with Huntington's disease, idiopathic torsion dystonia, tardive dyskinesia or off-dystonia in Parkinson's disease and most particularly for dyskinesia associated with movement disorders such as parkinsonism (e.g. idiopathic Parkinson's disease, post-encephalitic parkinsonism or parkinsonism resulting from head injury), treatment of schizophrenia, drug intoxication, manganese poisoning and the like.

The compounds may also be used in the treatment of dyskinesias which manifest as hyperkinetic activity (e.g. Tourette's syndrome).

The compounds are also useful for treatment of dyskinesias which arise as a side-effect of other therapeutic agents. For instance, the compounds are useful for the treatment of dyskinesia associated with ropinirole, pramipexole, cabergoline, bromcriptine, lisuride, pergolide, L-DOPA or apomorphine treatment. The compounds are preferably used for the treatment of dyskinesia associated with L-DOPA or apomorphine treatment.

The compounds are particularly useful for treating dyskinesia caused by agents used to treat movement disorders such as parkinsonism. In this respect a preferred use of the compounds is in the treatment of dyskinetic side-effects associated with L-DOPA or apomorphine therapy for parkinsonism.

The compounds may be used to treat existing dyskinesias but may also be used when prophylactic treatment is considered medically necessary. For instance, when it is considered necessary to initiate L-DOPA therapy and it is feared that dyskinesias may develop.

The compounds may be used to treat dyskinesia as a monotherapy (i.e. use of the compound alone); as an adjunct to medicaments to prevent dyskinetic side-effects caused by the medicament (e.g. as an adjunct to L-DOPA or apomorphine given to treat parkinsonian patients) or alternatively the compounds may be given in combination with other compounds or treatments which also reduce dyskinesia (e.g. μ-opioid receptor antagonists, $\alpha_2$-adrenoreceptor-antagonists, cannabinoid $CB_1$-antagonists, NMDA receptor-antagonists, GPi lesion/deep brain stimulation).

The compositions of the first and second aspects of the invention may take a number of different forms depending, in particular on the manner in which the composition is to be used. Thus, for example, the composition may be in the form of a powder, tablet, capsule, liquid, ointment, cream, gel, hydrogel, aerosol, spray, micelle, liposome or any other suitable form that may be administered to a person or animal. It will be appreciated that the vehicle of the composition of the invention should be one which is well tolerated by the subject to whom it is given and enables delivery of the compounds to the brain.

The composition of the invention may be used in a number of ways. For instance, systemic administration may be required in which case the compound may be contained within a composition which may, for example, be ingested orally in the form of a tablet, capsule or liquid. Alternatively, the composition may be administered by injection into the blood stream. Injections may be intravenous (bolus or infusion) or subcutaneous (bolus or infusion). The compounds may also be administered by inhalation (e.g. intranasally).

Compounds enhancing $H_3$-histamine receptor activity may also be administered centrally by means of intracerebral, intracerebroventricular, or intrathecal delivery.

The compound may also be incorporated within a slow or delayed release device. Such devices may, for example, be inserted under the skin and the compound may be released over weeks or even months. Such a device may be particularly useful for patients with long term dyskinesia such as patients on continuous L-DOPA therapy for the treatment of Parkinsonism. The devices may be particularly advantageous when a compound is used which would normally require frequent administration (e.g. at least daily ingestion of a tablet or daily injection).

It will be appreciated that the amount of a compound required is determined by biological activity and bioavailability which in turn depends on the mode of administration, the physicochemical properties of the compound employed and whether the compound is being used as a monotherapy or in a combined therapy. The frequency of administration will also be influenced by the above mentioned factors and particularly the half-life of the compound within the subject being treated.

Known procedures, such as those conventionally employed by the pharmaceutical industry (e.g. in vivo experimentation, clinical trials etc), may be used to establish specific formulations of compositions and precise therapeutic regimes (such as daily doses of the compounds and the frequency of administration).

Generally, a daily dose of between 0.01 μg/kg of body weight and 1.0 g/kg of body weight of a compound which enhances $H_3$-histamine receptor activity may be used for the treatment of dyskinesia depending upon which specific compound is used more preferably the daily dose is between 0.01 mg/kg of body weight and 100 mg/kg of body weight.

Purely by way of example a suitable dose of imetit for treating L-DOPA or chloro-APB induced dyskinesia in subjects with Parkinson's disease is between 0.1 mg/kg/day and 100 mg/kg/day (depending upon the health status of the individual). It is preferred that between 0.25 mg/kg/day and 20 mg/kg/day of imetit is given to a person daily. For instance it is most preferred that about 1-5 mg/kg/day imetit is given for treating dyskinesia induced by 0.2 mg/kg chloro-APB whereas about 5-20 mg/kg/day imetit is particularly effective for treating dyskinesia induced by 8 mg/kg L-DOPA.

It will be appreciated that the required dose will be effected by the route of administration. When imetit is given intravenously 0.1-10 mg/kg is a preferred dose whereas higher doses (e.g. 30 mg/kg) may be a suitable dose orally.

By way of further example suitable doses of 9-amino-1,2, 3,4-tetrahydroacridine and SKF91488 are preferably 0.5-30 mg/kg.

Daily doses may be given as a single administration (e.g. a daily tablet for oral consumption or as a single daily injection). Alternatively the compound used may require administration twice or more times during a day. As an example, imepip for treating L-DOPA induced dyskinesia in patients with Parkinson's disease may be administered as two (or more depending upon the severity of the dyskinesia) daily doses of between 25 mg and 5000 mg in tablet form. A patient receiving treatment may take a first dose upon waking and then a second dose in the evening (if on a two dose regime) or at 3 or 4 hourly intervals thereafter. Alternatively a slow release device may be used to provide optimal doses to a patient without the need to administer repeated doses.

A preferred means of using protein or peptide compounds which enhance $H_3$-histamine receptor activity for the treatment of dyskinesias is to deliver the compound to the brain by means of gene therapy. For instance, gene therapy may be used to increase expression of $H_3$-histamine receptors, increase expression of enzyme(s) responsible for the synthesis of endogenous $H_3$-histamine receptor agonists (e.g. histamine per se), decrease expression of a protein which promotes breakdown or desensitisation of $H_3$-histamine receptors or decrease expression of a protein which promotes breakdown of $H_3$-histamine receptor agonists. Therefore according to a fourth aspect of the present invention there is provided a delivery system for use in a gene therapy technique, said delivery system comprising a DNA molecule encoding for a protein which directly or indirectly enhances $H_3$-histamine receptor activity, said DNA molecule being capable of being transcribed to allow the expression of said protein and thereby treating a dyskinesia.

The delivery systems according to the fourth aspect of the invention are highly suitable for achieving sustained levels of a protein which directly or indirectly enhances $H_3$-histamine receptor activity over a longer period of time than is possible for most conventional therapeutic regimes. The delivery system may be used to induce continuous protein expression from cells in the brain that have been transformed with the DNA molecule. Therefore, even if the protein has a very short half-life as an agent in vivo, therapeutically effective amounts of the protein may be continuously expressed from the treated tissue.

Furthermore, the delivery system of the invention may be used to provide the DNA molecule (and thereby the protein which is an active therapeutic agent) without the need to use conventional pharmaceutical vehicles such as those required in tablets, capsules or liquids.

The delivery system of the present invention is such that the DNA molecule is capable of being expressed (when the delivery system is administered to a patient) to produce a protein which directly or indirectly has activity for enhancing $H_3$-histamine receptor activity. By "directly" we mean that the product of gene expression per se has the required activity. By "indirectly" we mean that the product of gene expression undergoes or mediates (e.g. as an enzyme) at least one further reaction to provide a compound effective for enhancing $H_3$-histamine receptor activity and thereby treating a dyskinesia.

The DNA molecule may be contained within a suitable vector to form a recombinant vector. The vector may for example be a plasmid, cosmid or phage. Such recombinant vectors are highly useful in the delivery systems of the invention for transforming cells with the DNA molecule.

Recombinant vectors may also include other functional elements. For instance, recombinant vectors can be designed such that the vector will autonomously replicate in the cell. In this case, elements which induce DNA replication may be required in the recombinant vector. Alternatively the recombinant vector may be designed such that the vector and recombinant DNA molecule integrates into the genome of a cell. In this case DNA sequences which favour targeted integration (e.g. by homologous recombination) are desirable. Recombinant vectors may also have DNA coding for genes that may be used as selectable markers in the cloning process.

The recombinant vector may also further comprise a promoter or regulator to control expression of the gene as required.

The DNA molecule may (but not necessarily) be one which becomes incorporated in the DNA of cells of the subject being treated. Undifferentiated cells may be stably transformed leading to the production of genetically modified daughter cells (in which case regulation of expression in the subject may be required e.g. with specific transcription factors or gene activators). Alternatively, the delivery system may be designed to favour unstable or transient transformation of differentiated cells in the subject being treated. When this is the case, regulation of expression may be less important because expression of the DNA molecule will stop when the transformed cells die or stop expressing the protein (ideally when the dyskinesia has been treated or prevented).

The delivery system may provide the DNA molecule to the subject without it being incorporated in a vector. For instance, the DNA molecule may be incorporated within a liposome or virus particle. Alternatively the "naked" DNA molecule may be inserted into a subject's cells by a suitable means e.g. direct endocytotic uptake.

The DNA molecule may be transferred to the cells of a subject to be treated by transfection, infection, microinjection, cell fusion, protoplast fusion or ballistic bombardment. For example, transfer may be by ballistic transfection with coated gold particles, liposomes containing the DNA molecule, viral vectors (e.g. adenovirus) and means of providing direct DNA uptake (e.g. endocytosis) by application of the DNA molecule directly to the brain topically or by injection.

Figure 2:
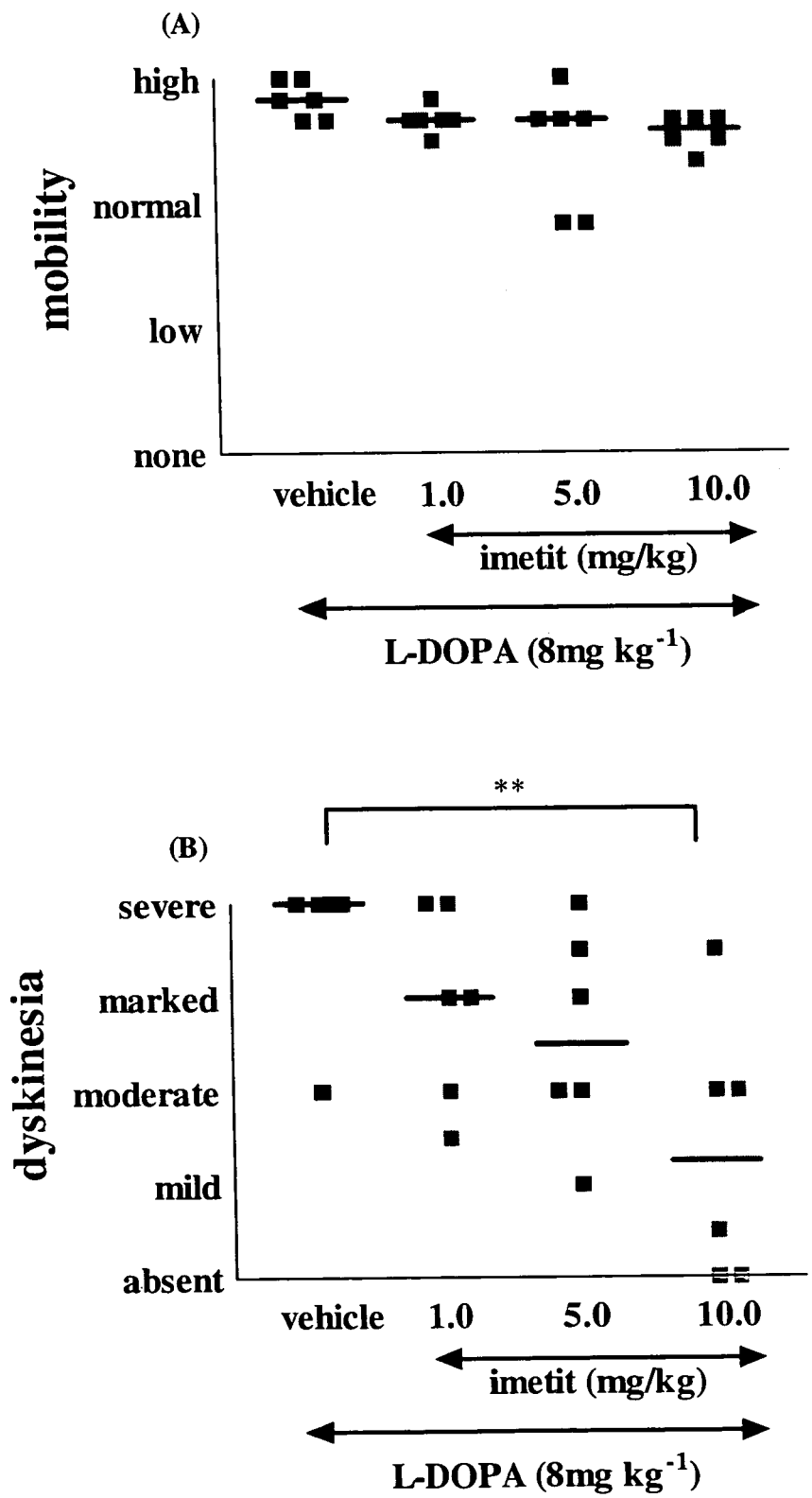

An embodiment of the present invention will now be described, by way of examples, with reference to the accompanying drawings, in which:

FIG. 1 is a graph illustrating the effect of the $H_3$-histamine receptor agonist imetit on hyperkinesia following chloro-APB treatment of parkinsonian rats (a rodent behaviour that is mechanistically equivalent to dyskinesia in primates) in Example 1; and FIG. 2 is a graph illustrating the effect of the $H_3$-histamine receptor agonist imetit on L-DOPA-induced mobility (A) and dyskinesia (B) in MPTP-lesioned marmosets of Example 2 wherein ** $P<0.01$ compared to L-DOPA+vehicle; non-parametric one-way repeated measures ANOVA (Friedman test) followed by Dunn's multiple comparison test.

EXAMPLE 1

The effect of the $H_3$-histamine receptor agonist imetit on dyskinesia was assessed in a reserpine-treated rat model of Parkinson's disease following treatment of the rats with the anti-parkinsonian agent chloro-APB (0.2 mg/kg).

1.1. Methods 1.1.1 Treatments.

Male Sprague-Dawley rats were split into two groups A and B. Rats in both groups were rendered parkinsonian by subcutaneous administration of reserpine (3 mg/kg) for 18 hours.

After the 18 hours Group A were treated with chloro-APB (0.2 mg/kg) and imetit (1 mg/kg) whereas B were treated with chloro-APB (0.2 mg/kg) and vehicle for imetit only.

1.1.2 Assessment of Activity and Mobility.

The locomotion of the rats in Groups A and B was measured over a one hour period using Benwick locomotor monitors. These locomotion monitors consist of a visually-shielded open-field arena, the perimeter of which is surrounded by a series of infra-red beams arranged at 5 cm intervals. PC-based software (Amlogger) assesses the number of beams broken. The number of beams broken as part of a locomotor movement (mobile counts) or the number of beam breaks while the animal is not locomoting (static counts) were measured. In addition, the system assesses the time for which animals are mobile or static.

1.2 Results

FIG. 1 illustrates that total mobile counts for imetit treated animals (A) was less than those treated with vehicle for imetit only (B). This demonstrates that there is a reduction in $D_1$-dopamine receptor-dependent locomotion (i.e. decreased activity via the direct striatal output pathway). In primates, dopamine D1 receptor stimulation of the direct pathway is a key mechanism in generating dyskinesia and thus the reduction observed with imetit is indicative of a decrease in dyskinesia (see the description).

EXAMPLE 2

The effect of the $H_3$-histamine receptor agonist imetit on L-DOPA-induced dyskinesia was assessed in the MPTP-lesioned marmoset model of Parkinson's disease.

2.1. Methods 2.1.1 Preparation of MPTP-Lesioned Marmoset Model of Parkinson's Disease Marmosets (*Callithrix jacchus*) (bred in a closed colony at the University of Manchester) are rendered parkinsonian by subcutaneous injection of 2 mg kg$^{-1}$ MPTP for 5 consecutive days. The marmosets are allowed to recover for a minimum of 10 weeks until their parkinsonism becomes stable. The degree of activity and disability before and after MPTP treatment is assessed using a combination of scales as described in section 2.1.2. Animals are then treated with L-DOPA for at least 3 weeks to prime them to elicit dyskinesia.

2.1.2 Assessment of Behaviour

Behaviour was assessed using the following scales:
 (a) Parkinsonian disability—non-parametric measures based on the following scales:
  Mobility score: 0=no movement, 1=movement of head on the floor of the cage, 2=movement of limbs, but no locomotion, on the floor of the cage, 3=movement of head or trunk on wall of cage or perch, 4=movement of limbs, but no locomotion, on wall of cage or perch, 5=walking around floor of cage or eating from hopper on floor, 6=hopping on floor of cage, 7=climbing onto wall of cage or perch, 8=climbing up and down the walls of the cage or along perch, 9=running, jumping, climbing between cage walls/perch/roof, uses limbs through a wide range of motion and activity.
 (b) Dyskinesia—non-parametric measures based on the following scale:
  Dyskinesia score: 0=Absent, 1=Mild, fleeting, 2=Moderate, not interfering with normal activity, 3=Marked, at times interfering with normal activity, 4=Severe, continuous, replacing normal activity.

The behavioural tests were assessed every 30 minutes for 4 hours, by post hoc analysis of video-recordings by an observer blinded to the treatment.

2.1.3 Treatments

Six marmosets received all treatments as described in table 1. The treatments were randomised such that on each day all six marmosets received one of the treatments. There was at least 48 hours washout between treatments.

TABLE 1

| Treatment number | Treatment | Route |
|---|---|---|
| 1 | L-DOPA (8 mg/kg) + vehicle | oral |
| 2 | L-DOPA (8 mg/kg) + imetit (1 mg/kg) | oral |
| 3 | L-DOPA (8 mg/kg) + imetit (3 mg/kg) | oral |
| 4 | L-DOPA (8 mg/kg) + imetit (10 mg/kg) | oral |

2.2. Results

FIG. 2 illustrates the effect of imetit treatment on L-DOPA-induced mobility (i) and dyskinesia (ii) in the MPTP-lesioned marmoset model of Parkinson's disease. These data demonstrate that imetit has no effect on L-DOPA-induced mobility. However, there is a dose-dependent reduction in the severity of L-DOPA-induced dyskinesia.

The MPTP-lesioned primate is the 'gold standard' preclinical model of Parkinson's disease. Therefore, these data are highly predictive of a beneficial therapeutic effect of $H_3$-histamine receptor agonists in the treatment of L-DOPA-induced dyskinesia in Parkinson's disease patients. Furthermore, these data suggest that the beneficial effect of imetit on L-DOPA-induced dyskinesia is not accompanied by a reduction in the therapeutic benefit of L-DOPA on mobility.

Although the data presented in these Examples demonstrate that $H_3$-histamine receptor agonists are useful for the treatment of dyskinesia associated with chloro-APB or L-DOPA therapy for Parkinson's disease, it will be appreciated that other compounds according to the present invention will be just as useful for treating other types of dyskinesias.

The invention claimed is:

1. A method of treating dyskinesia associated with dopamine replacement therapy comprising administering to a subject in need of such treatment a selective $H_3$-histamine receptor agonist, wherein the selective H3-histamine receptor agonist enhances $H_3$-histamine receptor activity or activation to a greater extent than the activity of other types of histamine receptors, thus treating dyskinesia associated with dopamine replacement therapy.

2. The method according to claim 1 wherein the $H_3$-histamine receptor agonist is selected from the group consisting of imetit, imepip and R(-)-alpha-methylhistamine.

3. The method according to claim 1 wherein said dyskinesia is associated with movement disorders.

4. The method according to claim 3 wherein said dyskinesia is associated with parkinsonism.

5. The method according to claim 4 wherein the parkinsonism is idiopathic Parkinson's disease or post-encephalitic parkinsonism.

6. The method according to claim 4 wherein the parkinsonism results from head injury, the treatment of schizophrenia, drug intoxication or manganese poisoning.

7. The method according to claim 1 wherein said dyskinesia is associated with Huntington's disease, idiopathic torsion dystonia, tardive dyskinesia or off-dystonia in Parkinson's disease.

8. The method according to claims 1 wherein said dyskinesia is a side-effect of a therapeutic agent.

9. The method according to claim 8 wherein said dyskinesia is associated with agents used to treat movement disorders.

10. The method according to claim 8 wherein the agent is L-DOPA, Chloro-APB or apomorphine.

11. The method according to claim 8 wherein the agent is used to treat parkinsonism.

12. The method according to claim 1 wherein said treatment is prophylactic treatment of dyskinesia.

13. The method according to claim 1 wherein said dyskinesia is associated with movement disorders and said $H_3$-histamine receptor agonist is imetit, imepip or R(-)-alpha-methylhistamine.

14. A combination therapeutic method of treating dyskinesia associated with dopamine replacement therapy comprising administering to a subject in need of such treatment a selective $H_3$-histamine receptor agonist, wherein the selective $H_3$-histamine receptor agonist enhances $H_3$-histamine receptor activity or activation to a greater extent than the activity of other types of histamine receptors, wherein the selective $H_3$-histamine receptor agonist is administered in combination with other compounds or treatments that reduce dyskinesia, thus treating dyskinesia associated with dopamine replacement therapy.

15. The method according to claim 14 wherein said other compounds comprise NMDA receptor-antagonists.

16. The method of claim 1, wherein the dopamine replacement therapy is for Parkinsonism or another basal ganglia-related movement disorder.

17. The method according to claim 1, wherein the dopamine replacement therapy comprises administration of L-DOPA or apomorphine.

18. The method according to claim 1, wherein the dyskinesia is L-DOPA-induced dyskinesia.

19. The method according to claim 1, wherein the dyskinesia is apomorphine-induced dyskinesia.

20. The method of claim 14, wherein the dopamine replacement therapy is for Parkinsonism or another basal ganglia-related movement disorder.

21. The method according to claim 14, wherein the dopamine replacement therapy comprises administration of L-DOPA or apomorphine.

22. The method according to claim 14, wherein the dyskinesia is L-DOPA-induced dyskinesia.

23. The method according to claim 14, wherein the dyskinesia is apomorphine-induced dyskinesia.

* * * * *